United States Patent [19]

Skakoon et al.

[11] Patent Number: 5,226,886
[45] Date of Patent: Jul. 13, 1993

[54] AMBULATORY TUBING SET WITH ANTI-SIPHON VALVE

[75] Inventors: James G. Skakoon, Melrose; Mitchell J. Palmer, Chelmsford, both of Mass.

[73] Assignee: Baxter International, Inc., Deerfield, Ill.

[21] Appl. No.: 804,895

[22] Filed: Dec. 6, 1991

[51] Int. Cl.⁵ .................. A61M 1/00; A61M 5/00
[52] U.S. Cl. .................. 604/153; 604/151; 604/247
[58] Field of Search .................. 604/151, 153, 31, 246, 604/247, 213

[56] References Cited

U.S. PATENT DOCUMENTS

| | | |
|---|---|---|
| 2,907,325 | 10/1959 | Burke . |
| 3,091,239 | 5/1963 | Moeller . |
| 4,187,057 | 2/1980 | Xanthopoulos . |
| 4,274,558 | 6/1981 | Clausen . |
| 4,347,874 | 9/1982 | Sullivan . |
| 4,515,589 | 5/1985 | Austin et al. .................. 604/153 |
| 4,650,471 | 3/1987 | Tamari .................. 604/153 |
| 4,687,468 | 8/1987 | Gianturco .................. 604/153 |
| 4,712,583 | 12/1987 | Pelmulder . |
| 4,798,590 | 1/1989 | O'Leary et al. .................. 604/153 |
| 4,828,551 | 5/1989 | Gertler et al. .................. 604/236 |
| 4,898,581 | 2/1990 | Iwatschenko . |
| 4,909,710 | 3/1990 | Kaplan et al. .................. 604/153 |
| 4,950,254 | 8/1990 | Andersen et al. .................. 604/247 |

OTHER PUBLICATIONS

Abbott Lab. Labels, "PCA Set, Mini-Bore with Integral Anti-Siphon Valve SL".
Abbott Lab. Labels, "PCA Continuous Infusion Set, Mini-Bore with Integral Anti-Siphon Valve-SL".

Primary Examiner—Gene Mancene
Assistant Examiner—Cindy A. Cherichetti
Attorney, Agent, or Firm—Kane, Dalsimer, Sullivan, Kurucz, Levy, Eisele and Richard

[57] ABSTRACT

An intravenous tubing set is provided with luer connectors, an anti-siphon valve and peristaltic pump engaging means. The anti-siphon valve will permit flow through the intravenous tubing set only when a preselected positive pressure as measured from the proximal end to the distal end of the anti-siphon valve is achieved.

2 Claims, 2 Drawing Sheets 5,226,886

AMBULATORY TUBING SET WITH ANTI-SIPHON VALVE

BACKGROUND OF THE INVENTION

1. Field of the Invention

This invention pertains to an ambulatory tubing set for use with a peristaltic pump, including an anti-siphoning means.

2. Background of the Invention

In the prior art, it is known to use a peristaltic pump in the infusion of pharmaceutical products so as to avoid contact between the pump and the pumped liquid. This maintains the sterility of the pharmaceutical product while avoiding the need for frequent washing of the peristaltic pump.

However, prior art solutions for preventing free flow of pharmaceutical product when the door of the peristaltic pump is inadvertently left open are deficient. These prior art solutions include such things as using a tubing clamp. This is deficient in that the clamp must be placed upon the tubing to stop the flow, and the same inadvertence that would result in the peristaltic pump door being left open is likely to result similarly in the failure to position properly the tubing clamp.

Several infusion tubing sets without peristaltic pump engaging means include anti-siphoning or check valves. However, these tubing sets are not adequate for use with a peristaltic pump.

OBJECTS AND SUMMARY OF THE INVENTION

It is therefore an object of this invention to provide an infusion tubing set for medical application which is adaptable to a peristaltic pump.

It is therefore a further object of this invention to provide an infusion tubing set for medical application for a peristaltic pump which will prevent free flow, back flow or siphoning when the door of the peristaltic pump is left open.

It is therefore a final object of this invention to provide an infusion tubing set for medical application with standard luer connections and an infusion tubing set with standard bag spike proximal connector.

These and other objects are effectively attained by providing a tubing set with proximal and distal luer connectors, and a tubing set with proximal bag spike and distal luer connector, a peristaltic pump engaging means, and an anti-siphon valve downstream of the peristaltic pump engaging means. The anti-siphon valve will permit flow only when there is a forward pressure differential greater than the opening pressure of the valve, such pressure being typically in the range of 1.5 to 3.5 pounds per square inch across the anti-siphon valve.

BRIEF DESCRIPTION OF THE DRAWINGS

Further objects and advantages of the invention will become apparent from the following description and claims, and from the accompanying drawings, wherein:

DETAILED DESCRIPTION OF THE PREFERRED EMBODIMENT

Figure 1:
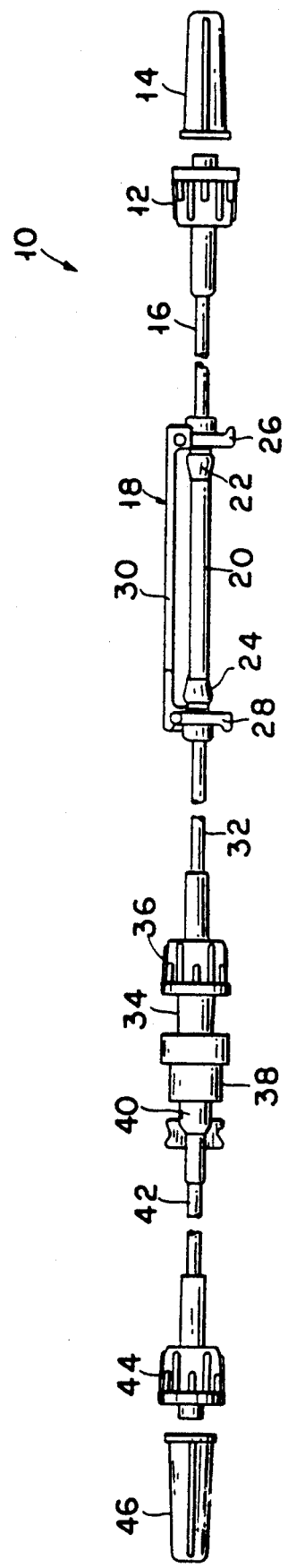
FIG. 1 is a plan view of the infusion tubing set of the present invention with a proximal luer connector.

Referring now to the drawings in detail wherein like numerals refer to like elements throughout the several views, one can see that FIG. 1 is a plan view of tubing set 10. Tubing set 10 includes proximal male luer connector 1 which is typically provided with vented female luer cap 14. Proximal male luer connector 12 is connected to a source of pharmaceutical product (not shown) thereby maintaining the proper flow direction through tubing set 10 and maintaining the proper orientation of the various components (to be described) of tubing set 10.

Figure 3:
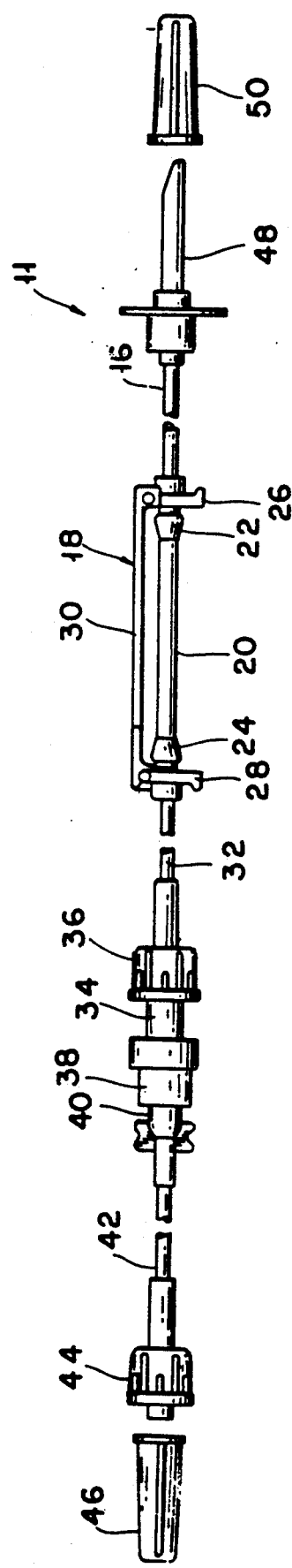
FIG. 3 is a plan view of the infusion tubing set of the present invention with a proximal bag spike connector.

FIG. 3 is a plan view of tubing set 11. Tubing set 11 includes proximal bag spike connector 48 which is typically provided with vented spike ca 50. Proximal bag spike connector 48 is connected to a source of pharmaceutical product (not shown) thereby maintaining the proper flow direction through set 11 and maintaining the proper orientation of the various components (to be described) of tubing set 11.

Figure 2:
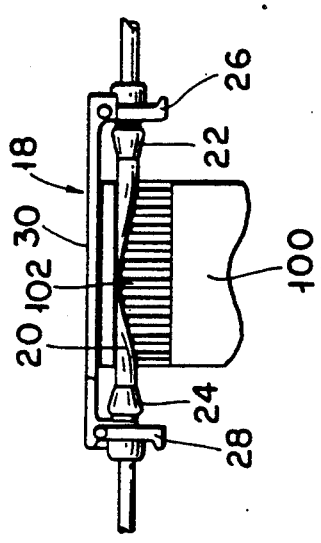
FIG. 2 is a plan view of the engagement of a portion of the infusion tubing set of the present invention to a peristaltic pump.

Tubing 16 provides fluid communication between proximal male luer connector 12 or proximal bag spike connector 48 and peristaltic pump engaging means 18. Peristaltic pump engaging means 18 includes silicon tubing 20. Silicon tubing 20 typically has an increased inner and outer diameter as compared to tubing 16 in order to increase the efficacy of the peristaltic pump 100 (see FIG. 2). Both ends of silicon tubing 20 are engaged by heat shrink tubing portions 22, 24, which, in turn, engage connectors 26, 28. Connectors 26, 28 engage the ends of pumping strap 30. As shown in FIG. 2, during operation, fingers 102 of peristaltic pump 100 press against silicon tubing 20 and pump liquid through tubing set 10.

Tubing 32 extends from connector 28 and is in fluid communication with tubing 16 and tubing 20. Tubing 32 leads to anti-siphoning valve 34 (an example of an appropriate anti-siphoning valve may be found in U.S. Pat. No. 4,535,820). Tubing 32 includes male luer connector 36 which is preferably permanently bonded by solvent to anti-siphoning valve 34. Similarly, the distal end of anti-siphoning valve 34 may include male luer connector 38 which engages female luer connector 40 which, in turn, is integral with tubing 42. Connectors 38 and 40 may be permanently joined to each other by solvent or similar means. Anti-siphoning valve 34 allows forward flow from proximal male luer connector 12 or proximal bag spike connector 48 only when a threshold forward pressure equal to the opening pressure of the valve (i.e., as measured from the proximal end of valve 34 to distal end of valve 34) of preferably from 1.5 to 3.5 pounds per square inch (gauge) is achieved.

Tubing 42 is integral with male luer connector 44. Male luer connector 44 is provided with a non-vented female luer cap 46 (note that cap 14 is preferably vented). However, when tubing set 10 or 11 is in use, male luer connector 44 is ordinarily attached to an intravenous needle or appropriate catheter (not shown).

To use tubing set 10 or 11, the user removes cap 14 and uses standard aseptic techniques to attach connector 12 or 48 to a source of pharmaceutical product and attach peristaltic pump engaging means 18 to peristaltic pump 100. The user then removes cap 46 and attaches an intravenous needle to connector 44. After properly setting peristaltic pump 100 and removing air from tubing set 10 or 11 and associated components, the intravenous needle or a catheter is inserted into the patient and the peristaltic pump 100 is operated. Obviously, those skilled in the art may see certain steps which may be reversed or, in the proper circumstances, even eliminated. Anti-siphoning valve 34 prevents flow through tubing set 10 or 11 except when a positive 2.5 pound per square inch pressure differential exists between the proximal end of valve 34 and the distal end of valve 34. This prevents improper free flow, back flow, or siphoning through tubing set 10 or 11.

Thus the several aforementioned objects and advantages are most effectively attained. Although only two preferred embodiments of the invention has been disclosed and described in detail herein, it should be understood that this invention is in no sense limited thereby and its scope is to be determined by that of the appended claims.

What is claimed is:

1. An infusion tubing set including:
   proximal connector means for receiving a pharmaceutical fluid;
   peristaltic pump engaging means coupled with and in fluid communication with said proximal connector means, said engaging means adapted to be coupled with a peristaltic pump for forcing the pharmaceutical fluid therethrough;
   anti-siphon valve means with a proximal end and a distal end, wherein the proximal end of said anti-siphon valve means is coupled with and is in fluid communication with said peristaltic pump engaging means; wherein said anti-siphon valve means allows flow of fluid therethrough only when a preselected positive pressure differential in the range of 1.5 to 3.5 pounds per square inch is achieved between said proximal end and said distal end thereof;
   distal connector means coupled with the distal end of the anti-siphon valve means for receiving fluid from said distal end of said anti-siphon valve means and transmitting said fluid to a patient;
   said proximal connector means and said distal connector means are luer connectors;
   tubing providing fluid communication between said proximal connector means and said peristaltic pump engaging means, between said peristaltic pump engaging means and said anti-siphon valve means, and between said anti-siphon valve means and said distal connector means; and
   said peristaltic pump engaging means includes a section of enlarged tubing with a larger inner diameter than an inner diameter of said tubing; and a pumping strap parallel with said enlarged tubing.

2. The infusion tubing set of claim 1 further including connecting means at ends of said enlarged tubing which are supported by said pumping strap.

* * * * *

UNITED STATES PATENT AND TRADEMARK OFFICE
CERTIFICATE OF CORRECTION

PATENT NO. :   5,226,886
DATED      :   July 13, 1993
INVENTOR(S):   James G. Skakoon and Michell J. Palmer It is certified that error appears in the above-identified patent and that said Letters Patent is hereby corrected as shown below:

Column 2, line 8, "1" should be --12--; and line 17, "ca" should be --cap--.

Signed and Sealed this

Tenth Day of May, 1994

Attest:

BRUCE LEHMAN

Attesting Officer    Commissioner of Patents and Trademarks